US009149019B2

(12) United States Patent
Everhart

(10) Patent No.: US 9,149,019 B2
(45) Date of Patent: Oct. 6, 2015

(54) METHOD OF ELIMINATING CAT URINE ODOR

(75) Inventor: William Curt Everhart, Castle Rock, CO (US)

(73) Assignee: JMR, LC, Urbandale, IA (US)

( * ) Notice: Subject to any disclaimer, the term of this patent is extended or adjusted under 35 U.S.C. 154(b) by 156 days.

(21) Appl. No.: 13/482,104

(22) Filed: May 29, 2012

(65) Prior Publication Data

US 2013/0323194 A1 Dec. 5, 2013

(51) Int. Cl.

| | |
|---|---|
| *A01K 1/01* | (2006.01) |
| *A01K 1/015* | (2006.01) |
| *A61L 9/04* | (2006.01) |
| *A61L 9/05* | (2006.01) |

(52) U.S. Cl.
CPC ............ *A01K 1/0107* (2013.01); *A01K 1/0152* (2013.01); *A61L 9/04* (2013.01); *A61L 9/044* (2013.01); *A61L 9/05* (2013.01); *A01K 1/0154* (2013.01); *A01K 1/0155* (2013.01)

(58) Field of Classification Search
CPC .... A61L 9/014; A01K 1/0155; A01K 1/0107; A01K 1/011
See application file for complete search history.

(56) References Cited

U.S. PATENT DOCUMENTS

| | | | |
|---|---|---|---|
| 6,180,092 B1 * | 1/2001 | Lagin | ............................ 424/76.4 |
| 6,797,235 B2 | 9/2004 | Boldt | |
| 7,726,260 B1 * | 6/2010 | Yananton | ........................ 119/171 |
| 2005/0175577 A1 * | 8/2005 | Jenkins et al. | ................ 424/76.1 |
| 2006/0045860 A1 | 3/2006 | Gupta | |
| 2006/0269472 A1 | 11/2006 | MacKinnon et al. | |

OTHER PUBLICATIONS

Faybutler, Permeability of Common Polymers (Plastics), (http://www.faybutler.com/pdf_files/HowHoseMaterialsAffectGas3.pdf), accessed Dec. 15, 2014.*
http://russerg.hubpages.com; Cat urine through the eyes of science 71; webpage article; printed Apr. 25, 2012; p. 1 of 1.
www.remove-cat-urine.com; The Composition of Cat Urine and Why this Recipe Works; webpage article; copyright 2008; p. 1 of 1.
www.cat-health-guide.org; The Cat Health Guide; product search Cat Urine; copyright 2012; webpages 1-7.
Squidoo LLC; www.squiddo.com; The Latest Medical and Surgical Technology, Saying By-Bye Cat Urine Smell; copyright 2012; webpages 1-4; Des Moines University Clinic, Des Moines, Iowa.
Wordpress How to Pro; product search Cat Urine Smell; copyright 2009 Cat Urine Smell; pp. 1-3; http://www.caturinesmellblog.com.
Cat World; All You Need to Know About Cats!; product search Urinalysis Test in Cats; copyright 2012 Cat World; webpages 1-6; Sydney Website Design; Sydney, Australia.
Wikipedia; product search Cat Pheromone; free online encyclopedia; pp. 1-3; last modified Feb. 11, 2012; Creative Commons Attribution-ShareAlike License.

* cited by examiner

*Primary Examiner* — Bethany Barham
*Assistant Examiner* — Barbara Frazier
(74) *Attorney, Agent, or Firm* — Zarley Law Firm, P.L.C.

(57) ABSTRACT

A method of eliminating cat urine odor. A CO2 generating mixture of carboxylic acid and a base is placed into a container and cat litter that is comprised of an absorbent material is placed over the top. During the deodorizing process of the cat urine, carbon dioxide is generated to enhance the deodorizing effect of the absorbent material.

9 Claims, 2 Drawing Sheets

METHOD OF ELIMINATING CAT URINE ODOR

BACKGROUND OF THE INVENTION

This invention is directed toward an odor elimination system. More specifically, this invention relates to a method of eliminating cat urine odor utilizing carbon dioxide.

Cats are domestic animals that individuals have as pets. Unlike other domesticated animals such as dogs that will stay close to a home or dwelling and/or can be fenced in, cats tend to roam and are able to climb. As a result in heavily populated areas cats must be kept indoors to avoid the hazards of vehicles, larger animals, and the like that can pose a danger to cats.

As a result of cats being house bound, litter boxes have been used for many years in order to keep a cat from going to the bathroom throughout a home or dwelling. In particular, litter is typically made of a material that is sand-like and additionally has a scent that attracts cats. Thus, as a result of a cat's natural instinct they will utilize the litter box preventing cat excrement from being all over the interior of a house.

While the invention of cat litter in a cat box has allowed cats to be easily domesticated, problems remain. In particular, cat urine has an extremely pungent odor. This odor is believed to be linked to the lack of water that cats drink. Typical cat urine consists of chemicals such as ammonia, sulphate, phosphate, chloride, sodium, creatinine, uric acid, urea and water. As a result of the ammonia, uric acid, urea and water a plurality of nitrogen, carbon, hydrogen and oxygen atoms are presented within the urine. As cat urine dries the urea and other chemicals are broken down by bacteria to form ammonia providing a very distinct smell. As time further passes the urine continues to decompose and thiols are formed emitting an even more pungent and unpleasant smell.

Cat litter currently used in the market is made of various materials that can include clay, bentonite, granulated bentonite clay, quartz or diatomaceous earth, zeolite, diatomite and sepiolite. Alternatively, biodegradable litters such as pinewood pellets, recycled newspaper, clumping sawdust, barley, dried orange peel, and the like can also be utilized. In particular, most of these cat litters have properties that allow the cat urine to be absorbed and cat feces to be covered to retain the urine the feces. Other materials take a further step such as zeolite that absorbs nitrogen and other chemicals and compounds within the cat urine in order to prevent the formation of ammonia and thiols as the cat urine breaks down.

While improvements to cat litter have been provided in order to cover up the smell and deodorize the cat litter itself, problems remain because after a period of time a cat litter box becomes saturated with urine and excrement leaving an undesirable odor associated therewith. In particular, even if the excrement is scooped from the cat litter, the cat urine still leaves a pungent smell causing the litter box to need to be changed within a week or two of initial use. Changing litter boxes is not only time consuming but additionally can be expensive. Thus, a need in the art exists for longer lasting cat litter.

Thus, a principal object of the present invention is to provide a method of eliminating cat urine odor.

Yet another object of the present invention is to sustain the life of litter materials without odor.

These and other objects, features, and advantages will become apparent from the specification and claims.

BRIEF SUMMARY OF THE INVENTION

A method of eliminating cat urine odor that include steps of placing a mixture of carbolic acid and a base in a container. Next, an absorbent material is placed within the container and nitrogen associated with the cat urine is absorbed within the absorbent material. In addition carbon dioxide is produced as a result of water vapor interacting with the mixture of the carbolic acid and the base to assist in the absorption of the nitrogen.

DETAILED DESCRIPTION OF THE PREFERRED EMBODIMENT

Figure 1:
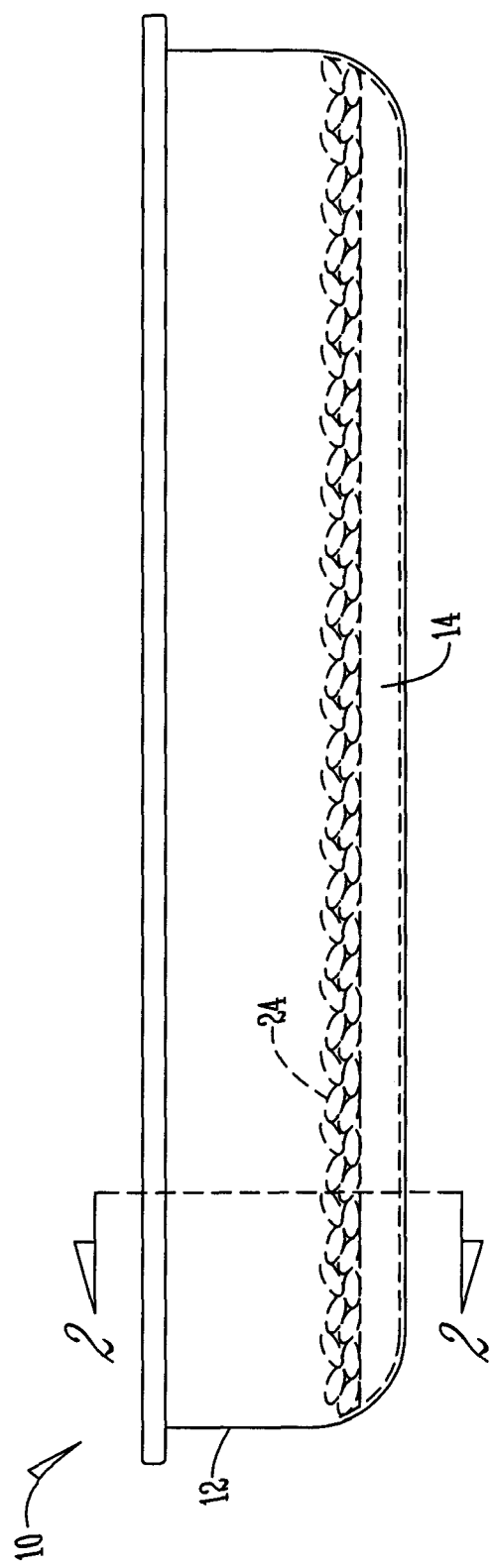
FIG. 1 is a side plan view of a cat urine elimination system.

The figures show a cat urine elimination system 10 that presents a container 12 that in a preferred embodiment is a cat litter box. While described as a container 12, a container 12 can be any body that holds cat litter including but not limited to, an opening in the ground, a cat litter box, cardboard box or the like. Disposed within the container 12 is a pad 14 that contains a mixture of a carboxylic acid and a base.

The composition contained within the pad comprises a mixture of a carboxylic acid and a base. The carboxylic acid can be any acid that, when reacted with a base, results in the production of carbon dioxide. The carboxylic acid can be aliphatic or aromatic.

Aliphatic acids include, but are not limited to, Formic acid, Acetic acid, Propionic acid, Butyric acid, Valeric acid, Caproic acid, Enanthic acid, Caprylic acid, Pelargonic acid, Capric acid, Propiolic acid, Vinylformic acid, Glyoxylic acid, Glycollic acid, 3-Butynoic acid, Crotonic acid, Vinylacetic acid, Pyruvic acid, Isobutyric acid, Oxalic acid, Lactic acid, trans-2-Penten-4-ynoic acid, Propargylacetic acid, Pent-2-enoic acid, Allylacetic acid, Isovaleric acid, Valeric acid, Malonic acid, alpha-Hydroxybutyric acid, 2-Methyllactic acid, 2-Furoic acid, Sorbic acid, trans,cis-2,4-Hexadienoic Acid, D,L-Propargylglycine, Acetylenedicarboxylic acid, Hydrosorbic acid, beta-Propylacrylic acid, Strawberiff (IFF), Maleic acid, Fumaric acid, Levulinic acid, Caproic acid, 3-Methyl Valeric acid, Succinic acid, 2-Heptenoic acid, cis-Hept-3-enoic acid, Methylenesuccinic acid, Oenanthic acid, Oxalacetic acid, Glutaric acid, Peroxyhexanoic acid, Malic acid, alpha-Toluic acid, Furylacrylic acid, trans,trans-Muconic acid, trans-Oct-2-enoic acid, cis-Oct-3-enoic acid, 4-Ethyl-hex-2-enoic acid, trans-3-Hexenedioic acid, Caprylic acid, 2-Ethylcaproic acid, alpha-Ketoglutaric acid, Phenylpropiolic acid, Adipic acid, D-Tartaric acid, Hydrocinnamic acid, p-Hydroxyphenylacetic acid, o-Hydroxyphenylacetic acid, (S)-Mandelic acid, (R)-Mandelic acid, cis-Non-3-enoic acid, alpha-Nonenoic acid, Pelargonic acid, Pimelic acid, 4-Phenyl-but-3-ynoic acid, Peroxyoctanoic acid, 4,6-Decadiynoic acid, p-Hydroxybenzoylformic acid, 4,6-Decadiyne-1,10-dioic acid, (R)-p-Hydroxymandelic acid, p-Hydroxymandelic acid, racemate, (S)-p-Hydroxymandelic acid, 4-Decynoic acid, 4-Ethyl-2-octenoic acid, Dec-3-enoic acid, 6-Acetoxy-5-hexenoic acid, 6-Acetoxy-4-hexenoic acid, 4-Ethylcaprylic acid, Capric acid, Aconitic acid, Suberic acid, 5-Phenyl-pent-4-ynoic acid, Vitamin C, alpha-Mercapto-caprylate, Diperoxyadipic acid, 4-Oxo-4-phenyl-butyric acid, 5-Phenyl Valeric acid, Hendecynoic acid, 5-Cyclohexyl-2-pentenoic acid, Cyclohexyl n-valerate, Undecylenic acid, 2-Hendenoic acid, 1-Naphthylacetic acid, trans-10-Hydroxy-dec-8-enoic Acid, Undecanoic acid, Azelaic acid, Peroxydecanoic acid, Benzo[1,3]dioxol-5-yl-propynoic Acid, Hexanoic acid, carboxy-hydroxy-methyl ester, Citric acid, Quinic acid, D-Gluconic acid, 10-Dodecynoic Acid, 9-Dodecynoic acid, 3-Dodecynoic Acid, 7-Dodecynoic acid, 8-Dodecynoic acid, 9-Dodecenoic acid, Dodec-2-enoic acid, 6-Dodecenoic acid, 7-Dodecenoic acid, 3-Methyl-undec-5-enoic acid, cis-5-Dodecenoic acid, 10-Dodecenoic Acid, 8-Dodecenoic acid, 3,8-Dimethyl-dec-5-enoic acid, Dodecli-enoic acid, AI3-05999, 9-Methyl-undecanoic acid, Lauric acid, 3 Methyl-undecanoic acid 4-Oxo-6-phenyl-hex-5-ynoic acid, beta-Naphthoxyacetic acid, Sebacic acid, alpha-Mercapto-caprate, 4-Oxo-6-phenyl-hexanoic acid, Galactaric acid, trans,trans-2,12-Tridecadienoic acid, 3,5-Dimethyl-undec-5-enoic acid, 12-Tridecenoic acid, trans-Tridec-2-enoic acid, 11-Methyl-dodecanoic acid, 10-Methyldodecanoic acid, Tridecylic acid, 12-Amino-dodecanoic acid, 2-(3-phenyl-prop-2-ynylidene)-malonic acid, Tetradeca-7,11-diene-5,9-diynoic Acid, alpha-Hydroxy-laurate, 8-Cyclohexyl-octanoic acid, 3-Ethyl-dodec-5-enoic acid, Tetradec-2-enoic acid, Myristoleic acid, cis,cis-5,8-Dihydroxy-2,6-dodecadienoic acid, 11-Methyl-tridecanoic acid, Myristic acid, Aseanostatin P1, Decamethylenedicarboxylic acid, alpha-Mercapto-laurate, Diperoxysebacic acid, cis-10-Pentadecenoic acid, 2-(2-Cyclopentyl-ethyl)-octanoic acid, 13-Methylmyristate, Sarcinic acid, Pentadecyclic acid, 1,13-Tridecanedioic acid, alpha-Hydroxymyristic acid, Decanoic acid, carboxy-hydroxy-methyl ester, 2-(3-Cyclopentenyl)-undecanoic acid, cis,cis-14-Methyl-5,9-pentadecadienoic acid, Palmitelaidic acid, 2-(2-Propenyl)-tridecanoic acid, 2-(2-Cyclopentyl-ethyl)-nonanoic acid, Palmitoleic acid, 2-(4-Cyclohexyl-butyl)-hexanoicacid, 2-(2-Cyclohexyl-ethyl)-octanoic acid, 2-Cyclopropylmethyl-dodecanoic acid, 2-Cyclohexylmethyl-nonanoic acid, trans-2-hexadecenoic acid, 2-Heptyl-2-nonenoic acid, 2-Butyl-dodecanoic acid, Palmitic acid, 14-Methylpentadecanoic acid, Anteisopalmitic acid, 2-Heptyl-nonanoic acid, 2-Hexyldecanoic acid 1,12-Dodecanedicarboxylic acid, alpha-Mercapto-myristate, 2-(3-Cyclopentenyl)-dodecanoic acid, 2-(2-Propenyl)-tetradecanoic acid, 2-(4-Cyclohexyl-butyl)-heptanoic acid, 2-Cyclobutylmethyl-dodecanoic acid, 2-(2-Cyclopentyl-ethyl)-decanoic acid, 2-(3-Cyclohexyl-propyl)-octanoic acid, 2-(2-Cyclohexyl-ethyl)-nonanoic acid, cis-10-Heptadecenoic acid, 2-(Methylcyclohexyl)-decanoic acid, 2-Butyl-12-tridecenoic acid, 2-(Methylcyclopropyl)-tridecanoic acid, 2-Cyclohexyl-undecanoic acid, cis,cis-8-Acetoxy-5-hydroxy-2,6-dodecadienoic acid, 15-Methylhexadecanoic acid, 2-Heptyl-decanoic acid, 14-Methylpalmitic acid, Margaric acid, 2-Hydroxypalmitic acid, gamma-Linolenic acid, Linolenic acid, alpha-Elaeostearic acid, beta-Elaeostearic acid, cis,cis-6,12-Octadecadienoic acid, 8-Octadecynoic acid, Isolinoleic acid, 10-Octadecynoic acid, 12-Octadecynoic acid, 14-Octadecynoic acid, 6-Octadecynoic acid, 4-Octadecynoic acid, cis,cis-7,12-Octadecadienoic acid, 2-Octadecynoic acid, 7-Octadecynoic acid, cis,cis-5,12-Octadecadienoic acid, cis,cis-8,12-Octadecadienoic acid, 5-Octadecynoic acid, 17-Octadecynoic acid, Chaulmoogric acid, 13-Octadecynoic Acid, 15-Octadecynoic acid, 11-Octadecynoic acid, Linolelaidic acid, Linoleic acid, trans, trans-10,12-Octadecdienoic acid, Cilienic acid, cis,cis-6,10-Octadecadienoic acid, 9-Stearolic acid, 2-(2-Cyclohexyl-ethyl)-4-cyclohexyl-butanoic acid, Oleic acid, trans-10-Octadecenoic Acid, Dihydrochaulmoogric acid, 14-Octadecenoic acid, 15-Octadecenoic acid, 17-Octadecenoic acid, 2-(2-Cyclohexyl-ethyl)-decanoic acid, cis-5-Octadecenoic acid, 2-(4-Cyclohexyl-butyl)-octanoic acid, 2-Octyl-2-decenoic acid, 2-Cyclohexyl-dodecanoic acid, 2-(2-Propenyl)-pentadecanoic acid, cis-12-Octadecenoic acid, cis-Vaccenic acid, Octadec-2-enoic acid, trans-Vaccenic acid, Petroselinic acid, 4-Octadecenoic acid, Petroseladic acid, trans-12-Octadecenoic acid, Isooleic acid, 2-(3-Cyclohexyl-propyl)-nonanoic acid, cis-7-Octadecenoic acid, cis-8-Octadecenoic acid, 2-Cyclopentyl-tridecanoic acid, cis-13-Octadecenoic acid, Elaidic acid, cis-2-Methoxy-5-hexadecenoic acid, 11-Cyclohexyl-9-hydroxy-undecanoic acid, cis-2-Methoxy-6-hexadecenoic acid, 2-Ethylhexadecanoic acid, Stearic acid, Isostearic acid, 15-Methyl-heptadecanoic acid, Tridecanoic acid, carboxy-hydroxy-methyl ester, alpha-Mercapto-palmitate, 9,10-Epoxylinolenic acid, 9-Hydroxylinolenic acid, 13-Hydroxylinolenic acid, 16-Hydroxylinolenic acid, 270. 15-Epoxylinolenic acid, 2-(2-Cyclopent-2-enyl-ethyl)-dodecanoic acid, 5-Cyclohexyl-2-(2-cyclohexyl-ethyl)-pentanoic acid, Ricinstearolic acid, 12-Epoxylinoleic acid, 13-Hydroxylinoleic acid, Lactisaric acid, 9-Hydroxylinoleic acid, 9-Epoxylinoleic acid, cis-7-Nonadecenoic acid, trans-7-Nonadecenoic Acid, 2-Cyclohexyl-tridecanoic acid, Ricinoleic acid, Ricinelaidic acid, Oxidooleic acid, trans-8-(3-Octyl-oxiranyl)-octanoic Acid, Nonadecylic acid, 17-Methyloctadecanoic acid, 16-Methyloctadecanoic acid, 12-Hydroxy-stearic acid, alpha-Hydroxystearic acid, Arachidonic acid, Pulvic acid, Arachidic acid, 3RS,7R,11R-Phytanic acid, 18-Methyl-nonadecanoic acid, 9,10-Dihydroxy-stearic acid, alpha-Mercapto-stearate, 9-Oxo-13-prostenoic acid, Cibaric acid, Protolichesterinic acid, 9-Oxoprostanoic acid, Cervonic acid, Hexadecanoic acid, carboxy-hydroxy-methyl ester, trans-9,12,13-Trihydroxy-10-octadecenoic Acid, Clupanodonic acid, 9,10,12-Trihydroxy-stearic acid, Erucic acid, Brassidic acid, Acetyl aleuritolic acid, Sativic acid, alpha-Disulfodicaprylate, Nervonic acid, Rangiformic acid, cis-6,7,8-Triacetoxy-5-hydroxy-2-decenoic acid, alpha-Disulfodicaprate, Laricic acid, alpha-Disulfodilaurate, 2-Amino-succinic acid, 1-(4-octadecanoyloxy-butyl)ester, alpha-Disulfodimyristate, alpha-Disulfodipalmitate, and alpha-Disulfodistearate.

Aromatic acids include, but are not limited to, Benzoic acid, Anthranilic acid, m-Salicylic acid, Salicylic acid, p-Salicylic acid, Anisic acid, m-Anisic acid, 6-Methylsalicylic acid, o-Anisic acid, 4-Amino-salicylic acid, Protocatechuic acid, gamma-Resorcylic acid, alpha-Resorcylic acid, beta-Resorcylic acid, o-Pyrocatechuic acid, Gentisic acid, Piperonylic acid, Terephthalic acid, Phthalic acid, 3-Formyl-4-hydroxy-benzoic acid, 3-Ethyl-2-hydroxy-benzoic acid, Isovanillic acid, o-Vanillic acid, p-Osellinic acid, 4-Methoxysalicylic acid, Orsellic acid, Vanillic acid, 5-Methoxy-salicylic acid, Pyrogallolcarboxylic acid, Phloroglucinic acid, Gallic acid, Acetylsalicylic acid, 6-Hydroxy-benzo[1,3]diox-ole-5-carboxylic acid, Monoperphthalic acid, 3,5-Dimethoxy-benzoic acid, 2,5-Dimethoxybenzoic acid, Veratric acid, 2,6-Dimethoxybenzoic acid, beta-Orcincarboxylic acid, o-Veratric acid, 3,5-Dihydroxy-p-anisic acid, alpha-Hydroxynaphthalic acid, beta-Hydroxynaphthalic acid, Divaric acid, Syringic acid, 3,4-Dimethoxy-5-hydroxybenzoic acid, 4,6-Dimethoxysalicylic acid, Oxy-beta-Ocrincarboxylic acid, 4-(5-Hydroxy-pentyl)-benzoic acid, 6-Pentyl-salicylic acid, 2-Acetylaminogentisic acid, 2,4,5-Trimethoxybenzoic acid, Eudesmic acid, 2,4,6-Trimethoxybenzoic acid, o-Phenoxy-benzoic acid, m-Phenoxybenzoic acid, Taboganic acid, Olivetolic acid, 4-(5-Hydroxy-pentyloxy)-benzoic acid, 3-Hydroxy-5-phenoxy-benzoic acid, 2-(2-Hydroxy-phenoxy)-benzoic acid, 3-(3-Hydroxy-phenoxy)-benzoic acid, 4'-Hydroxy-3-phenoxybenzoic acid, 5-Hexyl-2,4-dihydroxy-benzoic acid, p,p'-Diphenic acid, 3-(4-Methoxy-phenoxy)-benzoic acid, 2-(3-Phenyl-propynoyl)-benzoic acid, 6-Octyl-salicylic acid, 2-(4-Carboxy-phenoxy)-benzoicacid, Olivetonic acid, 4-(5-Carboxy-3-hydroxy-phenoxy)-benzoic Acid, 6-Decyl-salicylic acid, 3,7-Dihydroxy-dibenzofuran-1,9-dicarboxylic acid, 6-Dodecyl-salicylic acid, Lecanoric acid, Anacardic acid, 6-[8(Z),11(Z)-Pentadecadienyl]salicylic acid, 6-[8(Z)-Pentadecenyl]salicylic acid, 6-Pentadecyl-salicylic acid, Parellic acid, 2,4-Dihydroxy-6-pentadec-8-enyl-benzoic acid, cis,cis,cis-2-Heptadeca-3,6,9-trienyl-6-hydroxy-benzoic acid, cis,cis-2-Heptadeca-6,9-dienyl-6-hydroxy-benzoic acid, Protocetraric acid, cis-2-Heptadec-10-enyl-6-hydroxy-benzoic acid, Divaricatic acid, cis-2-Hydroxy-6 nonadec-12-enyl-benzoic acid, Sphaerophorin, 6-Eicosyl-salicylic acid, 2-(10-Acetoxy-pentadec-8-enyl)-4, 6-dihydroxy-benzoic acid, Anziaic acid, cis-2-Heneicos-15-enyl-6-hydroxy-benzoic acid, alpha-Collatolic acid, and Microphyllic acid.

In a preferred embodiment, the carboyxlic acid is citric acid. The base can be any base that, when reacted with a carboxylic acid, results in the production of carbon dioxide. Preferably, the base is a carbonate, bicarbonate, tricarbonate, etc. More preferably, the base is a metal carbonate, metal bicarbonate, metal tricarbonate, etc. Examples of such carbonates, bicarbonates, and tricarbonates, etc. include, but are not limited to, calcium carbonate, sodium carbonate, lithium carbonate, potassium carbonate, calcium bicarbonate, sodium bicarbonate, lithium bicarbonate, potassium bicarbonate, etc. In a most preferred embodiment, the base is sodium bicarbonate.

Figure 2:
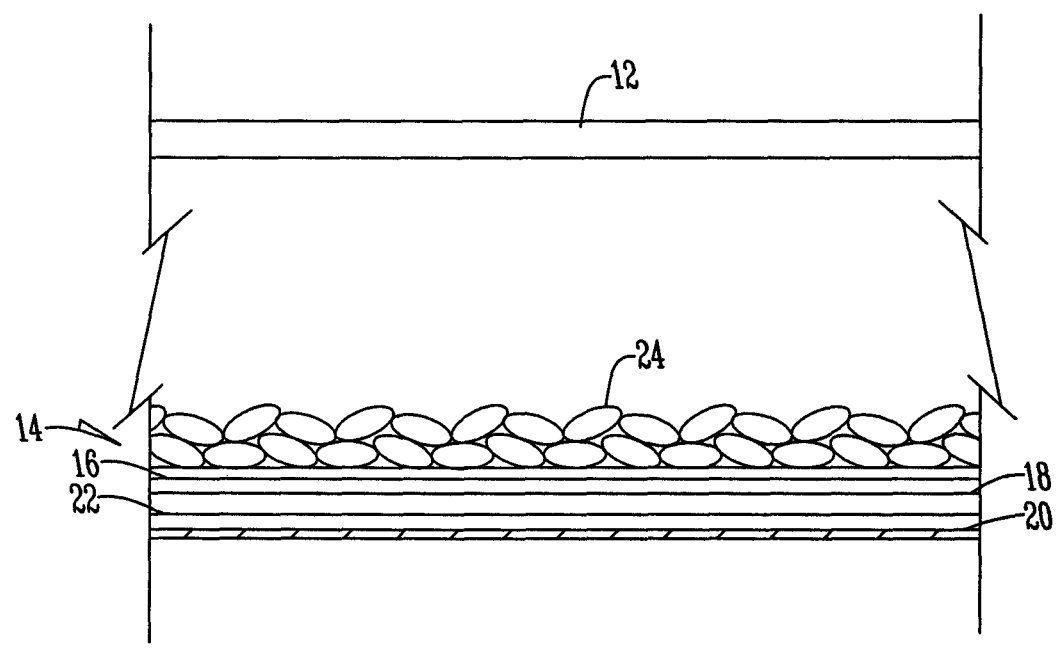
FIG. 2 is a sectional view of a cat urine elimination system.

In one embodiment as shown in FIG. 2 the pad 14 comprises first and second gas permeable layers 16 and 18 and a liquid permeable layer 20 that in a preferred embodiment is perforated plastic. The first and second gas permeable layers 16 and 18 are made of a material that allows at least gas to pass through; however, in addition liquids and/or solids may additionally pass through. In a preferred embodiment the gas permeable layers 16 and 18 only allow the passage of gas such as water vapor therethrough and will not allow the passage of liquid such as liquid water or solids such as ice to pass through the layers.

As best seen in FIG. 2 while first and second gas permeable layers 16 and 18 can be used additional gas permeable layers 22 can be added to the pad without falling outside the scope of this disclosure. In particular, each gas permeable layer 16, 18 and 22 in one embodiment contains the mixture of a carboyxlic acid and base. In a preferred embodiment this mixture is provided in a solid or powdered form. In addition, the pad 14 is placed within the container 12 and in a preferred embodiment extends the length of the bottom of the container to receive a urine absorbing material 24 thereon. The urine absorbing material in one embodiment is cat litter and in another embodiment is an agent placed or sprinkled on cat litter. In one embodiment the cat litter is zeolite and in another embodiment the agent is zeolite.

In operation, a container 12 is provided and a pad 14 having the mixture of carboxylic acid and base are placed into the container 12. The urine absorbing material 24 is then placed on top of the pad 14 within the container 12. When a cat urinates in the container 12 the urine absorbing material 24 absorbs nitrogen and other molecules in the cat urine. Meanwhile, as a result of water in the cat urine or water vapor the pad 14, and in particular, the mixture of the carboxylic acid and base will begin generating carbon dioxide that interacts with the urine absorbing material 24 and the urine itself. In particular, the carbon dioxide eliminates cat urine odor in two separate manners. First, the carbon dioxide slows the growth of bacterial that breaks down the urea and other compounds within the cat urine to prevent ammonia and thiols from forming. In addition, the oxygen molecules within the carbon dioxide similarly bond to thiols and with hydrogen molecules in order to neutralize the by-products of the breakdown of the cat urine.

Thus provided is a cat urine eliminating system 10 that utilizes a pad that produces carbon dioxide to enhance the effects of absorbent material 24 to capture the ingredients of cat urine that creates odor while eliminating the ingredients that do not create the odor. As a result, cat litter that previously was only able to last a week can now last 30 days before the absorbent material 24 is saturated or the CO2 producing mixture stops being effective. Thus, as a result the life of the cat litter increases eliminating the amount of times the litter must be changed thus saving time and reducing cost. Thus at the very least all of the stated objectives have been met.

What is claimed is:

1. A method of eliminating cat urine odor steps comprising:
    placing a pad having at least three gas permeable layers but liquid impermeable in a container wherein at least one gas permeable layer contains a mixture of a citric acid and a sodium bicarbonate;
    placing a urine absorbing material within the container;
    placing zeolite on the urine absorbing material;
    absorbing urine within the urine absorbing material; and
    permitting an effective amount of water vapor from the urine to permeate the gas permeable layers such that the water vapor reacts with the mixture of citric acid and sodium bicarbonate to produce an effective amount of carbon dioxide to react with and neutralize the urine.

2. The method of claim 1 wherein the mixture of the citric acid and the sodium bicarbonate is a dry powder.

3. The method of claim 1 wherein the container is a cat litter box.

4. The method of claim 1 wherein the three gas permeable layers prevent liquid from passing therethrough and contacting the mixture of the citric acid and the sodium bicarbonate.

5. The method of claim 1 wherein all gas permeable layers contain the mixture of the citric acid and the sodium bicarbonate.

6. The method of claim 1 wherein the mixture of the citric acid and the sodium bicarbonate is solid.

7. A method of eliminating cat urine odor steps comprising:
    placing a pad having a gas permeable layer that is liquid impermeable in a container wherein the gas permeable layer contains a mixture of citric acid and sodium bicarbonate;
    placing a urine absorbing material within the container;
    absorbing urine within the urine absorbing material; and
    permitting an effective amount of water vapor from the urine to permeate the gas permeable layer such that the water vapor reacts with the mixture of citric acid and sodium bicarbonate to produce an effective amount of carbon dioxide to react with and neutralize the urine absorbed by the urine absorbing layer 8. The method of claim 1 wherein the effective amount of carbon dioxide prevents ammonia and thiols from forming in the urine.

9. The method of claim 1 wherein the effective amount of carbon dioxide bonds to thiols and hydrogen molecules to neutralize by-products of broken down urine.

* * * * *